(12) United States Patent
Polosa et al.

(10) Patent No.: US 9,103,057 B2
(45) Date of Patent: Aug. 11, 2015

(54) NONWOVEN CALENDERED FABRICS

(71) Applicant: SUOMINEN CORPORATION, Helsinki (FI)

(72) Inventors: Gianluca Polosa, Helsinki (FI); Roberto Pedoja, Helsinki (IT)

(73) Assignee: SUOMINEN CORPORATION, Helsinki (FI)

( * ) Notice: Subject to any disclaimer, the term of this patent is extended or adjusted under 35 U.S.C. 154(b) by 3 days.

(21) Appl. No.: 13/955,010

(22) Filed: Jul. 31, 2013

(65) Prior Publication Data

US 2014/0037906 A1    Feb. 6, 2014

(30) Foreign Application Priority Data

Jul. 31, 2012   (IT) ............... MI2012A1340

(51) Int. Cl.

| | | |
|---|---|---|
| *D04H 3/16* | (2006.01) | |
| *D04H 1/49* | (2012.01) | |
| *D04H 3/013* | (2012.01) | |
| *D04H 3/007* | (2012.01) | |
| *D04H 3/005* | (2012.01) | |
| *D04H 3/009* | (2012.01) | |
| *D04H 3/011* | (2012.01) | |
| *D04H 1/54* | (2012.01) | |
| *D04H 3/11* | (2012.01) | |
| *D04H 3/14* | (2012.01) | |
| *D04H 5/03* | (2012.01) | |
| *D04H 5/06* | (2006.01) | |

(Continued)

(52) U.S. Cl.
CPC ............ *D04H 1/49* (2013.01); *A61F 13/15577* (2013.01); *B32B 23/00* (2013.01); *D04H 1/54* (2013.01); *D04H 3/005* (2013.01); *D04H 3/007* (2013.01); *D04H 3/009* (2013.01); *D04H 3/011* (2013.01); *D04H 3/013* (2013.01); *D04H 3/11* (2013.01); *D04H 3/14* (2013.01); *D04H 5/03* (2013.01); *D04H 5/06* (2013.01); *D06C 23/04* (2013.01); *Y10T 428/2457* (2015.01)

(58) Field of Classification Search
CPC ....... D04H 3/005; D04H 3/007; D04H 3/009; D04H 3/011; D04H 3/013; D04H 3/11; D04H 3/16
USPC .................. 264/103, 210.2; 28/104
See application file for complete search history.

(56) References Cited

U.S. PATENT DOCUMENTS

| 4,451,520 A | 5/1984 | Tecl et al. |
|---|---|---|
| 5,151,320 A | 9/1992 | Homonoff et al. |

(Continued)

FOREIGN PATENT DOCUMENTS

| DE | 10004448 A1 | 7/2001 |
|---|---|---|
| EP | 1939341 A1 | 7/2008 |

(Continued)

OTHER PUBLICATIONS

Albrecht, Fuchs, Kittelmann, Nonwoven Fabrics, XP-002691349, Jan. 1, 2003, p. 191, ISNB:3-527-30406-1, Wiley-VCH, Weinheim.

*Primary Examiner* — Leo B Tentoni
(74) *Attorney, Agent, or Firm* — Nixon & Vanderhye P.C.

(57) ABSTRACT

Nonwoven calendered materials for various applications such as household use and personal and hygienic care are provided. In particular, the present invention can be applied to the manufacture of wipes and cleaning cloths. Methods for making and using nonwoven calendered fabrics are also provided.

12 Claims, 11 Drawing Sheets

(51) Int. Cl.
  *D06C 23/04* (2006.01)
  *B32B 23/00* (2006.01)
  *A61F 13/15* (2006.01)

(56) References Cited

U.S. PATENT DOCUMENTS

| | | |
|---|---|---|
| 5,208,098 A | 5/1993 | Stover |
| 5,244,482 A | 9/1993 | Hassenboehler, Jr. et al. |
| 5,964,742 A | 10/1999 | McCormack et al. |
| 6,610,390 B1 | 8/2003 | Kauschke et al. |
| 2004/0199134 A1* | 10/2004 | Mizutani et al. ............... 604/367 |
| 2005/0085149 A1 | 4/2005 | Sommer |
| 2006/0266473 A1 | 11/2006 | Senapati et al. |
| 2007/0143976 A1 | 6/2007 | Sommer |
| 2008/0318487 A1 | 12/2008 | Pedoja |
| 2009/0004942 A1 | 1/2009 | Pedoja |

FOREIGN PATENT DOCUMENTS

| | | |
|---|---|---|
| WO | 2010039579 A1 | 4/2010 |
| WO | 2012130414 A1 | 10/2012 |

* cited by examiner

NONWOVEN CALENDERED FABRICS

CROSS-REFERENCE TO RELATED APPLICATION

This application claims priority to and benefit of Italian Patent Application No. MI2012A001340 filed Jul. 31, 2012, the contents of which are incorporated by reference in their entirety.

FIELD OF THE INVENTION

The present invention relates to the field of non-woven textile products are applied to the manufacture of nonwoven fabrics, particularly nonwoven products for various applications such as household use, personal and hygienic care. In particular, the present invention can be applied to the manufacture of wipes and cleaning cloths.

BACKGROUND OF THE INVENTION

Wet or impregnated wipes are of wide application in several fields. For example, nonwoven fabric cloths are used for cleaning purposes and may be impregnated with waxes or other cleaning solutions. Wet wipes are also used for personal care and may contain detergents, perfumes or even cosmetic lotions or creams.

These products are normally made from cellulose-based raw materials (typically less than 50% cellulose), such as pulp, carded viscose/lyocell airlace or spunlace, cotton and the like, which are provided with absorbent properties.

High absorbent properties are necessary for the cloth to be moistened and to retain a sufficient amount of the type of solution of the desired type (detergent, cosmetic and so on).

The above raw material fibers are generally hydroentangled or firmly bonded and are wetted with a solution of detergent and/or perfume, so that they can be packaged ready for use.

Pulp, viscose and lyocell absorb high amounts of water into the fiber. A stack of wet wipes with these fibers tends to be dense and thus its height is less than for similar wipes containing thermoplastic fibers such as polypropylene and polyester. As wet wipes are commonly packed in flexible plastic packagings, a small stack of wipes will give customers a negative impression of the amount of material in the package. Additionally, a softer wipe is more desirable by the customer due to its better feel.

Moreover, a certain amount of polypropylene, polyester or the like is normally added to this kind of product. The presence of such thermoplastic materials in the composition of a wipe is contrary to the aim of providing biodegradable products.

Biodegradability is considered an important feature for a wet wipe. The nature of these products implies that they should be flushable. Therefore, it is normally required that a flushable product be biodegradable.

However, biodegradability is not the only requirement that should be ideally fulfilled when providing a flushable wipe. As waste waters are normally made to pass through pumps, particularly when they must move against the force of gravity, for example, when they reach wastewater treatment plants, the material should also be water dispersible to avoid blockage of such pumps by the solid mass.

Improved water dispersibility can be achieved, but unfortunately this occurs by sacrificing the strength of the material. Biodegradability implies a long period of exposure to environmental conditions but water dispersibility is needed quickly. While looking at known products on the market, a good balance between water dispersibility and mechanical strength is still a great and long-felt need in this field.

It should be noted that a mechanical stress on a sheet of nonwoven material develops along two preferential directions that are perpendicular one to the other: the MD (Machine Direction) and the CD (Cross Direction). The MD is the direction along which the material is processed: a high strength along this direction prevents the sheet from being torn during the production of the wipes. The CD direction, conversely, is the direction along which the wipe is dispensed by the packaging, i.e. the direction along which the customer pull the wipe out, as required by current packaging processes. A good strength along this direction is essential as well. It is therefore important that a good balance between MD and CD strengths is obtained. This is also a great and long-felt need in the nonwoven fabric industry.

SUMMARY OF THE INVENTION

It is therefore an object of the present invention to provide nonwoven fabric materials that are biodegradable.

It is a further object of the invention to provide nonwoven fabric materials that are sufficiently water dispersible so that they can be used as flushable products.

Another object of the invention is to provide nonwoven fabric materials having improved mechanical properties and in particular a good balance between MD and CD strength.

A further object of the invention is to provide nonwoven fabric materials having good softness and an appreciable height even when wet.

Another object of the invention is to provide wet wipes having a good appearance and a balanced MD/CD strength ratio which are also flushable.

Further objects of the invention include methods for making the above nonwoven fabric materials.

Further characteristics and the advantages of the present invention will be better understood from the following detailed description of non-limiting representative embodiments with reference to the Figures briefly described below.

DETAILED DESCRIPTION

In certain embodiments, nonwoven fabric materials according to the present invention include material having at least one layer of long fibers or of continuous filaments of a biodegradable material.

The term "biodegradable material" herein may include either biodegradable material as such or compostable material.

In certain embodiments, the nonwoven fabric material may be a multi-layered material having at least one layer of long fibers or of continuous filaments of a biodegradable material and at least one layer of fibers of a water-absorbent material.

Long fibers in the material may vary between about 20% and about 100% by weight.

In certain embodiments, nonwoven fabric materials may be multi-layered material having at least one layer of long fibers or of continuous filaments of a biodegradable material and at least one layer of short fibers or shortcut fibers of the same or of a different material.

The term "long fibers" herein includes fibers having a length that may vary from about 4 mm to about 60 mm, and in certain embodiments from 15 to 40 mm.

The term "short fibers" herein includes fibers having a length that may vary from substantially 0, i.e. powder, to 2.5 mm, and in certain embodiments from 1 to 2 mm.

The term "shortcut fibers" herein includes fibers having a length that may vary from about 5 to about 10 mm.

The term "continuous filament" generally includes a filament of a polymer obtained by the spunbond technique. In certain embodiments, continuous filaments may have a diameter between about 0.5 dtex and about 6.7 dtex, and in certain embodiments a diameter of between about 0.9 and about 2.5 dtex.

Representative examples of long fiber material include viscose, lyocell, polylactic acid (PLA), optionally as a bicomponent fiber, biopolymers from cereals or plant fibers and mixtures thereof.

The term "bicomponent fiber" includes a fiber obtained by co-extrusion of two different polymers. These are also known as "conjugate fibers". Representative examples of bicomponent filament configurations include sheath-core (concentric or eccentric), side-by-side (equal or unequal portions), and islands-in-a-sea.

Representative examples of short fibers material include cellulose pulp, cotton and mixtures thereof.

Representative examples of shortcut fiber material include viscose, lyocell and synthetic fibers. The term "synthetic fibers" includes fibers of polyester and polypropylene.

Representative examples of continuous filaments material include continuous filaments of polylactic acid (PLA).

In certain embodiments, nonwoven fabric materials of the invention may include an amount of polylactic acid greater than about 5% by weight, in certain embodiments greater than about 10% by weight, and in other embodiments greater than 30% by weight.

In certain embodiments, nonwoven fabric materials of the invention may include an amount of long fibers material in the range of about 40% to about 60% by weight. In certain embodiments, the amount of cellulose pulp in the nonwoven fabric material may be in the range of about 40% to about 60% by weight.

In certain embodiments, the nonwoven fabric material of the invention may include a total amount of long fibers material and cotton of about 100% by weight (in which no cellulose pulp is contained).

In certain embodiments, the nonwoven fabric material of the invention may include a total amount of 100% of long fiber material.

In certain embodiments, the nonwoven fabric material of the invention contains an amount of continuous filaments of spunbond PLA, or of a web of a biopolymer as described above, between about 40% and about 50% by weight, the remaining part being cellulose pulp.

In certain embodiments, nonwoven fabric material of the invention may include an amount of continuous filament of spunbond PLA, or of a web of a biopolymer as described above, having between about 40% and about 50% by weight which may be further provided with a hydrophilic coating, and which may be obtained by treatment of the nonwoven fabric material with wetting additives.

The wetting additives may include those commonly employed in the field, such as cationic, anionic or non-ionic surfactants.

In certain embodiments, an anionic surfactant may be used as a wetting agent. Such anionic surfactant may include an alkyl-polyglucoside ester. In one embodiment, the said alkyl polyglucoside ester may be selected from disodium cocopolyglucose sulphosuccinate, disodium cocopolyglucose citrate, sodium cocopolyglucose tartrate or mixtures thereof. These surfactants are associated with the trademarks EUCAROL® AGE SS, EUCAROL® AGE EC and EUCAROL® AGE ET, respectively, and are commercially available from LAMBERTI spa. In the course of testing, small amounts of this additive provided high levels of absorption capacity to the final product. In fact, the low dosage addition of additives leads to improved quality of the products as compared with other products obtained with high dosages, as will be discussed in more detail below.

The basis weight of nonwoven fabric materials may be in the range of between about 20 and about 60 g/m$^2$. In particular, basis weight of between about 30 and about 60 g/m$^2$ may be preferred, and a basis weight of between about 40 and about 50 g/m$^2$ may be particularly preferred in certain embodiments.

When nonwoven fabric materials are provided with a hydrophilic coating, its basis weight may be in the range of between about 20 and about 40 g/m$^2$.

In certain embodiments, nonwoven fabric materials may have a web structure that includes more than one web, for example, 3 to 9 webs. With 3-9 webs, a more isotropic textile structure, and accordingly a maximized spatial layout of the fibers or filaments can be achieved, which provides an increased fabric-water contact surface. This allows water droplets to be adsorbed by the structure within the small spaces resulting from the random distribution of the fibers or filaments.

In certain embodiments, nonwoven fabric materials may include a tri-layered material having one internal layer of water-absorbent, flushable material, and one upper and lower layer of long fibers or continuous filaments of a biodegradable material, in order to create a sandwich structure.

Nonwoven fabric materials may be produced using processes having the following general steps:
a) Depositing on a support at least one layer of a biodegradable material in the form of long fibers or continuous filaments;
b) Depositing on the support or on the layer of step a) at least one layer of water-absorbent, flushable material;
c) Hydroentangling the layers and drying the hydroentangled material;
d) Calendering the dried material of step c) to create a calendered pattern which process is able to provide a balanced ratio of MD/CD average tensile strength to the nonwoven fabric material in the range of about 1:1 to about 4:1.

The long fibers or continuous filaments of step a) may include those described above.

Spunbond filaments may be produced along with the formation of the nonwoven fabric material or alternatively can be made on a separate production line.

Spunbond filaments may be produced through extrusion by spinnerets of the above described polymer materials so as to form continuous filaments. After production of such filaments, they may be hit by a jet of compressed air that causes the elongation and the electrostatic charging thereof such as to cause a mutual repulsion causing them to fall randomly onto a support (i.e. a conveyor belt). The continuous filament may be obtained by a spinning process by means of 1- to 5-orifices, and in certain embodiments 2-3 orifices.

In certain embodiments, step b) may include depositing a material in the form of short fibers as described above.

The hydroentanglement step c) can be a conventional process, that provides a so-called spunlace web structure. This process provides for entanglement of the web fibers, moving on a perforated or patterned screen, through the use of high-pressurized water jets. The water pressure generally increases from the first to the last injectors, and pressures up to 2200 psi may be used to direct the water jets onto the web. The impinging of the water jets on the web promotes entanglement of the fibers. Exhaust water may be removed by vacuum from the screen, to avoid flooding of the web. The free water being entrapped among the fibers may be eliminated by drying.

The drying step may be performed, for example, in a drying oven. The temperature within the oven depends on the speed at which the product passes through and may be adjusted such that complete evaporation of the water is ensured. For example, if a product with 55 g/m$^2$ grammage is typically produced at 150 m/min, the temperature within the oven may be set at about 120° C. for complete water evaporation.

The calendering step is an important step in the present invention. The basic function of the calendaring step is to bond partially the fibers/filaments of the nonwoven fabric and to cut the long fibers in order to weaken the strength of the material.

One of the two rollers, in the calender, may be engraved, i.e. it may have ribs in the form of dots or dashes evenly alternating with grooves. The shape, distribution and dimension of the dots and of the grooves strongly influences the mechanical properties of the material. In fact, it has been found that the calendering pattern according to embodiments of the invention (see FIGS. 7 and 7A) provides to the nonwoven fabric an improved balanced ratio of MD/CD average tensile strength when compared to different calendering patterns according to the prior art (see FIG. 8).

The ratio of MD/CD average tensile strength for nonwoven fabric material of the invention may be in the range of about 1:1 to about 4:1. In certain embodiments, the MD/CD average tensile strength ratio is in the range of about 1:1 to about 3:1. Moreover, the MD/CD average tensile strength ratio reaches particularly advantageous values when the nonwoven fabric material is wet or moistened, so that values between about 1:1 and about 2:1 are achieved.

Particular embodiments of the calendering pattern according to the invention are shown in FIGS. 7-7A and 9-9A.

Calendering pattern may include a plurality of ribs 20 that are shaped like a stretched S (stretched-S-shaped). In particular, the shape of these ribs may include a first tract having a first curvature and a second tract having a second curvature being the opposite of the first curvature, the first and the second tracts being joined by a flexion point. The phrase "a second curvature being the opposite of the first curvature" means that if the first curvature is concave, the second curvature is convex, or vice versa.

In certain embodiments, the angle γ formed between a line tangential to one of the two ends of a rib and a line tangential to the flexion point may be from about 15° to about 25°, and in certain embodiments is about 20°.

In certain embodiments, the ribs have a height H between about 0.5 and about 0.9 mm, and in certain embodiments about 0.7 mm. certain embodiments provide a free head T with a contact surface area for the fabric from about 4 mm$^2$ to about 10 mm$^2$, in certain embodiments from about 5 mm$^2$ to about 8 mm$^2$, and a distribution so that it covers about 6 to about 18%, and in certain embodiments about 8 to about 17%, of the surface of the roller.

Figures 7, 7A:
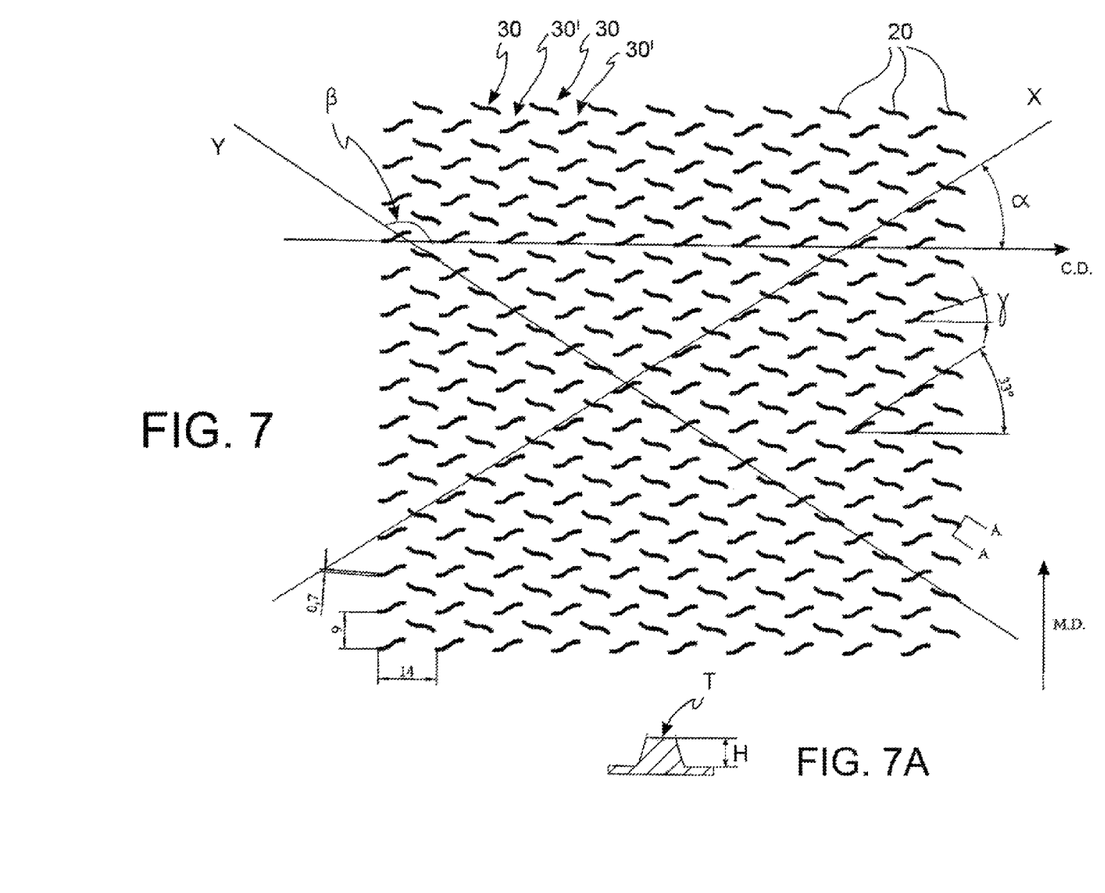
FIG. 7 illustrates a calendering pattern according to embodiments of the invention.
FIG. 7A illustrates a section along the direction A-A of a detail of the engraving pattern of FIG. 7.
Figures 9, 9A:
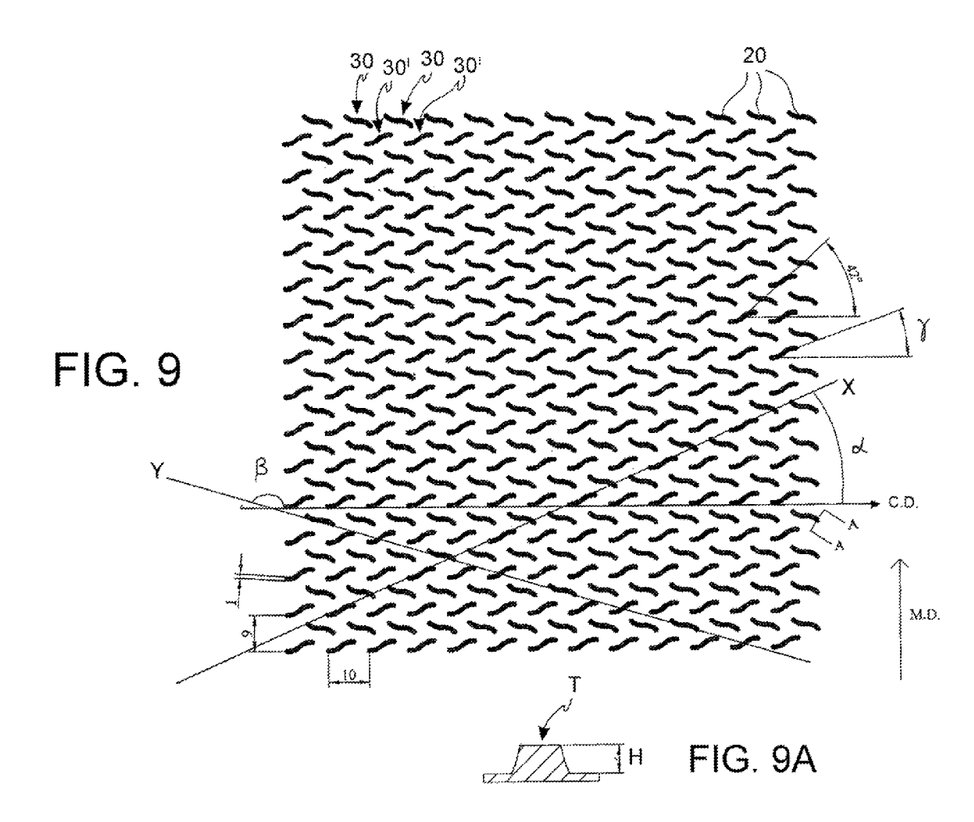
FIG. 9 illustrates another calendering pattern according to the invention.
FIG. 9A illustrates a section along the direction A-A of a detail of the engraving pattern of FIG. 9.

The ribs 20 may be arranged in rows along the machine direction (MD). Each row may form first modules 30 and second modules 30' in alternate alignment. Two first modules 30 that are separated by a second module 30' may be described as "close modules". Analogously, two second modules 30' that are separated by a first module 30 also may be described as "close modules".

In each of the first modules 30 the ribs 20 may be inclined and have the same orientation, i.e. they may form the same angle with the cross direction (CD). However, each first module 30 may be adjacent to two second modules 30' having an opposite orientation, i.e. these latter form angles, with respect to the CD, that are supplementary to the angles formed by the first modules 30. In this way, diagonal lines X and Y are defined joining corresponding points of the ribs 20 in first modules 30 or second modules 30', which diagonal lines define the inclined orientation of the ribs 20 in such first modules 30 or second modules 30', respectively.

A first angle α may be formed between the diagonal line X, defining the inclined orientation of the ribs in the first modules 30, and the cross-direction (CD), this angle α being less than about 45°. In certain embodiments, this angle α is in the range of between about 27° and about 39°, and in certain embodiments between about 31° and about 35°, and in still other embodiments about 33°.

Consequently, a second angle β may be formed between the diagonal line Y, defining the inclined orientation of the ribs 20 in the second modules 30' and the cross-direction (CD), this second angle β being supplementary to the first angle α and being more than about 135°, and in certain embodiments between about 153° and about 141°, and in still other embodiments between about 149° and about 145°, and in still further embodiments about 147°.

As stated above, the distribution of the ribs 20 in the calendering pattern is an important feature. In certain embodiments, the pitch between corresponding points of adjacent ribs 20 in a same first or second module 30, 30' may be between about 7 and about 12 mm, and in certain embodiments about 9 mm. Conversely, the pitch between corresponding points of ribs 20 in two close first modules 30 or in two close second modules 30' may be between about 8 and about 16 mm, and in certain embodiments between about 10 and about 14 mm.

FIGS. 10-10A and 11-11A show alternative calendering patterns of alternative embodiments.

Figures 10, 10A:
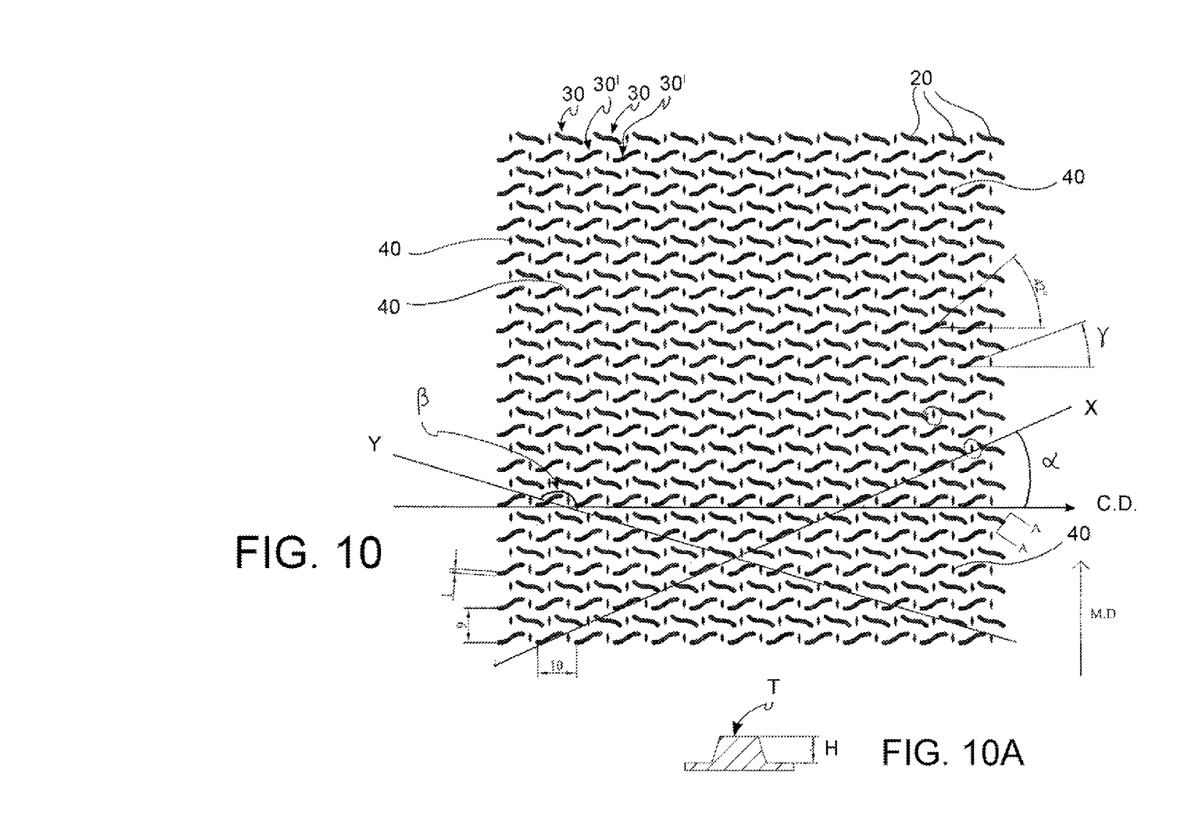
FIG. 10 illustrates still another calendering pattern according to the invention.
FIG. 10A illustrates a section along the direction A-A of a detail of the engraving pattern of FIG. 9.

The pattern shown in FIGS. 10-10A is the same as that of FIGS. 9-9A, but in addition presents a plurality of dots 40 of elongated shape, which may be interposed between the ribs 20 in close rows of the first and second modules 30, 30', respectively. The elongated dots 40 may be aligned along the MD direction. As a result of such elongated dots 40, the total percentage of the surface of the roller covered by ribs 20 and dots 40 may be about 18 to about 25%, and in other embodiments about 19%.

Figures 11, 11A:
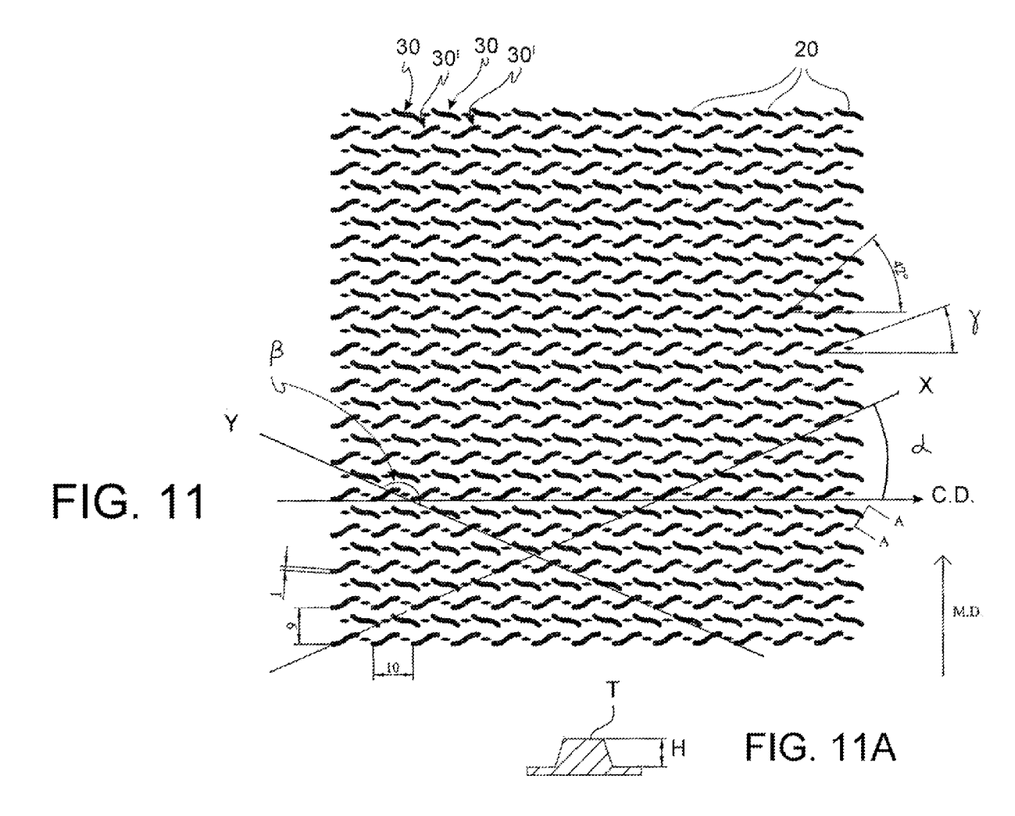
FIG. 11 illustrates still another calendering pattern according to the invention.
FIG. 11A illustrates a section along the direction A-A of a detail of the engraving pattern of FIG. 9.

The pattern shown in FIGS. 11-11A may be the same as that of FIGS. 10-10A, but the elongated dots 40 may be aligned along the CD direction.

The calendering step may be performed at a temperature in a range from about 0° C. to about 150° C., and at a nip pressure in a range of about 25 to about 100 N/mm, and in certain embodiments between about 30 and about 70 N/mm.

In certain embodiments, processes of the invention may include a wetting step to confer hydrophilic properties to the material. The wetting step may include treating nonwoven fabric materials with wetting additives as described above.

The wetting step may be performed, for example, between the hydroentanglement step and the drying step.

The wetting treatment method may include those used in common practice, such as, for example:
  spraying: the product mixture may be sprayed on the fibers;
  coating: the product mixture may be applied by a contact roller spreading the products on the web surface;
  printing: the same as coating, but using a printing machine;
  impregnation; the web structure, either already built up or in an intermediate step, may be dipped in a mixture of selected products, then the excess amount may be wrung by means of a mangle or similar systems;
  foam coating: a mixture of selected products may be mixed with a gas (usually air) in a high speed agitator until its physical state is that of a foam, and the foam then may be applied to the web by conventional coating techniques.

The dosage of the wetting additive may change as a function of the fibers being used, based on features such as density, distribution, etc. and desired level of adsorption (e.g. the amount of adsorbed, retained water and the adsorption time, capillarity).

Nonwoven fabric materials of the invention also may be provided with various additives.

Several types of additives may be added to the synthetic fibers or continuous filaments by the manufacturers or otherwise, such as: lubricating additives to give smoothness and easy processability; antistatic additives to prevent damaging electrostatic currents that may degrade the product reduce the productivity of the machine; anti-foam additives to avoid the generation of foam, especially at the hydro-entanglement step.

In certain embodiments, the processes according to the present invention also may include one or more of the following final steps in addition to the ones described above, in order to increase or add additional characteristics to the end product: e.g. coloring or finishing of a chemical nature such as anti-pilling treatment, improvement of flame proof properties, substantially mechanical treatments such as napping, sanforizing, emerizing and the like.

Such processes also may include a final step of winding the nonwoven fabric material to make a fabric bobbin.

The invention now will be further described by means of exemplary embodiments, with further reference to FIGS. 1-8. These figures do not show stations for adding the above-described additional substances, however such stations are conventional and can be positioned at any point along the production line, such as before the last bonding step.

Figure 1:
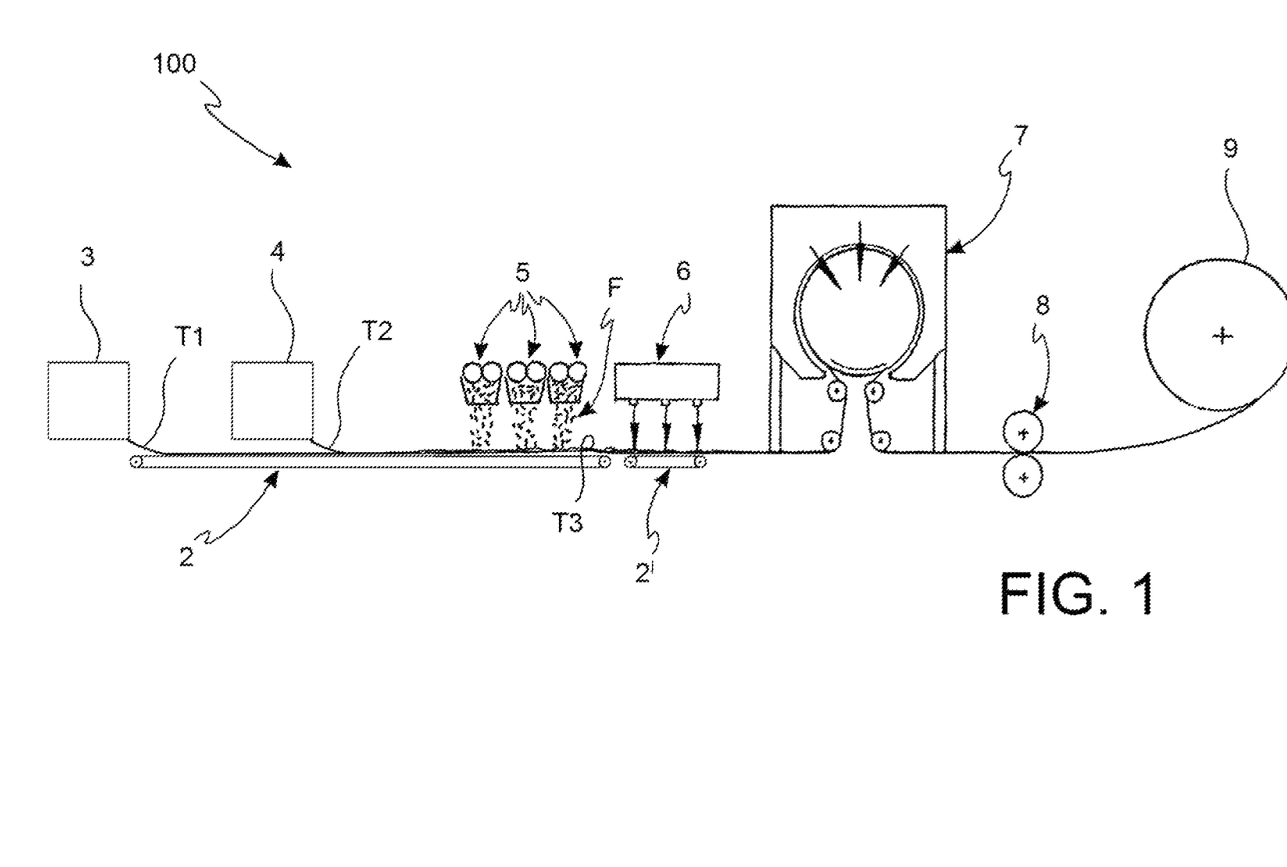
FIG. 1 illustrates by way of a schematic view a method for making nonwoven fabrics according to embodiments of the invention.

FIG. 1 shows a first embodiment of a production line 100 for manufacturing materials according to the present invention.

On transporting elements 2, such as a conveyor belt, a layer T1 of long fibers as described above may be deposited in the form of a carded web by a feeding line 3. A second layer T2 of short fibers (e.g. cotton fibers) may be fed in the form of a carded web by a second feeding line 4.

Subsequently, water-absorbent, short fibers F, such as cellulose pulp fibers, may be laid through suitable dispensing elements 5 to form a layer T3.

The web structure so-created may include from about 40 to about 60% by weight of layers T1 and T2 taken together and from about 60 to about 40% by weight of water-absorbent, short fibers.

After deposition of water-absorbent, short fibers, the layered material may be passed on to second transporting elements 2' through hydroentangling processes 6 such as those of a conventional type.

Bonded nonwoven fabric then may be dried passing through drying elements 7.

The dried nonwoven fabric may be subjected to calendering by calender 8 which has the calendering pattern depicted in FIG. 7.

Finally, bonded nonwoven fabric materials may be wound on a receiving bobbin 9.

Figure 2:
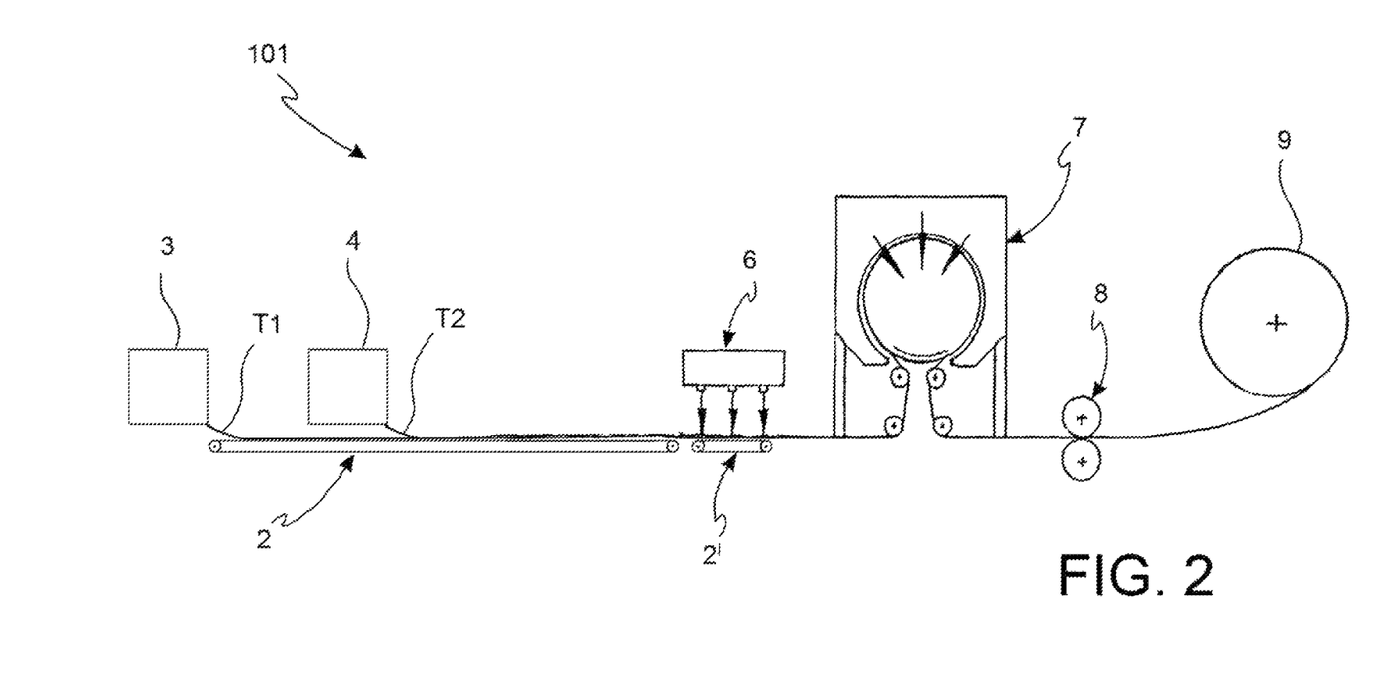
FIG. 2 illustrates by way of a schematic view a method for making nonwoven fabrics according to further embodiments of the invention.

FIG. 2 shows a second embodiment of a production line 101 for manufacturing the materials according to the present invention.

On transporting elements 2, such as a conveyor belt, a layer T1 of long fibers as described above may be deposited in the form of a carded web by a feeding line 3. A second layer T2 of short fibers (e.g. cotton fibers) may be fed in the form of a carded web by a second feeding line 4.

The sum of the amounts of layers T1 and T2 may be about 100% by weight of the nonwoven fabric.

The layered material then may be passed on to second transporting elements 2' through hydroentangling processes 6 such as those of a conventional type.

Bonded nonwoven fabric then may be dried passing through drying elements 7.

Dried nonwoven fabric may be subjected to calendering by the calender 8 which has the calendering pattern shown in FIG. 7.

Finally, bonded nonwoven fabric materials may be wound on a receiving bobbin 9.

Figure 3:
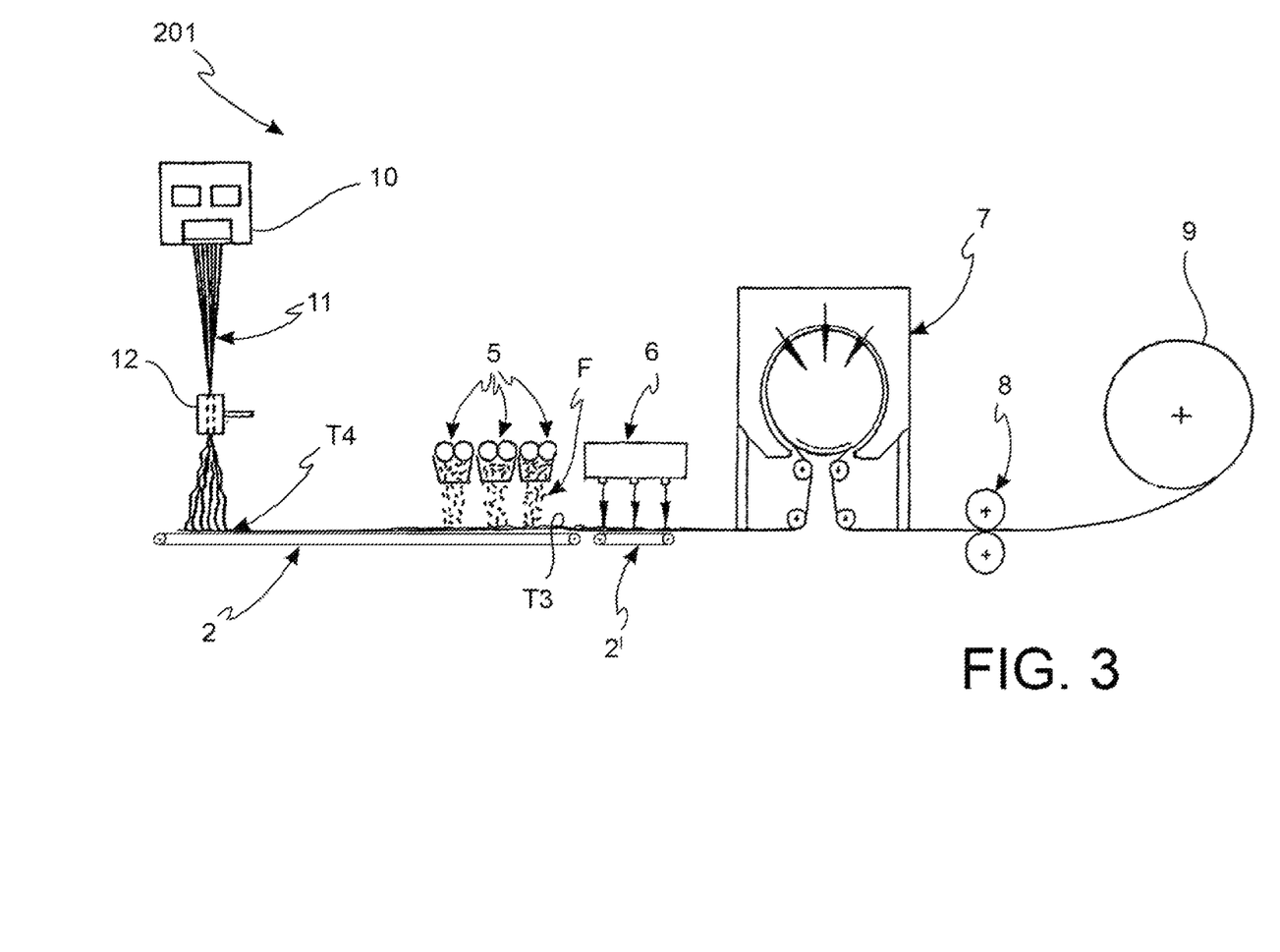
FIG. 3 illustrates by way of a schematic view a method for making nonwoven fabrics according to still further embodiments of the invention.

FIG. 3 shows a third embodiment of a production line 201 for manufacturing the inventive materials according to the present invention.

On a transporting elements 2, such as a conveyor belt, a layer T4 of continuous filaments as described above (e.g. PLA spunbond filaments) may be deposited after being extruded by a suitable spinneret 10. The threads 11 exiting the orifices of the spinneret 10 may be made to pass through a suction fan 12 positioned underneath the spinneret 10, in order to suck and convey the individual threads of extruded polymer in order to favor the bonding thereof into a single filament.

Subsequently, water-absorbent, short fibers F, such as cellulose pulp fibers, may be deposited through suitable dispensing elements 5 to form a layer T3.

The web structure so-created may include from about 40 to about 50% by weight of continuous filaments and from about 50 to about 40% by weight of water-absorbent, short fibers.

The layered material then may be passed on to second transporting elements 2' through hydroentangling processes 6 such as those of a conventional type.

The bonded nonwoven fabric then may be dried passing through drying elements 7.

The dried nonwoven fabric may be subjected to calendering by the calender 8 which may have the calendering pattern depicted in FIG. 7.

Finally, the bonded nonwoven fabric material may be wound on a receiving bobbin 9.

Figure 4:
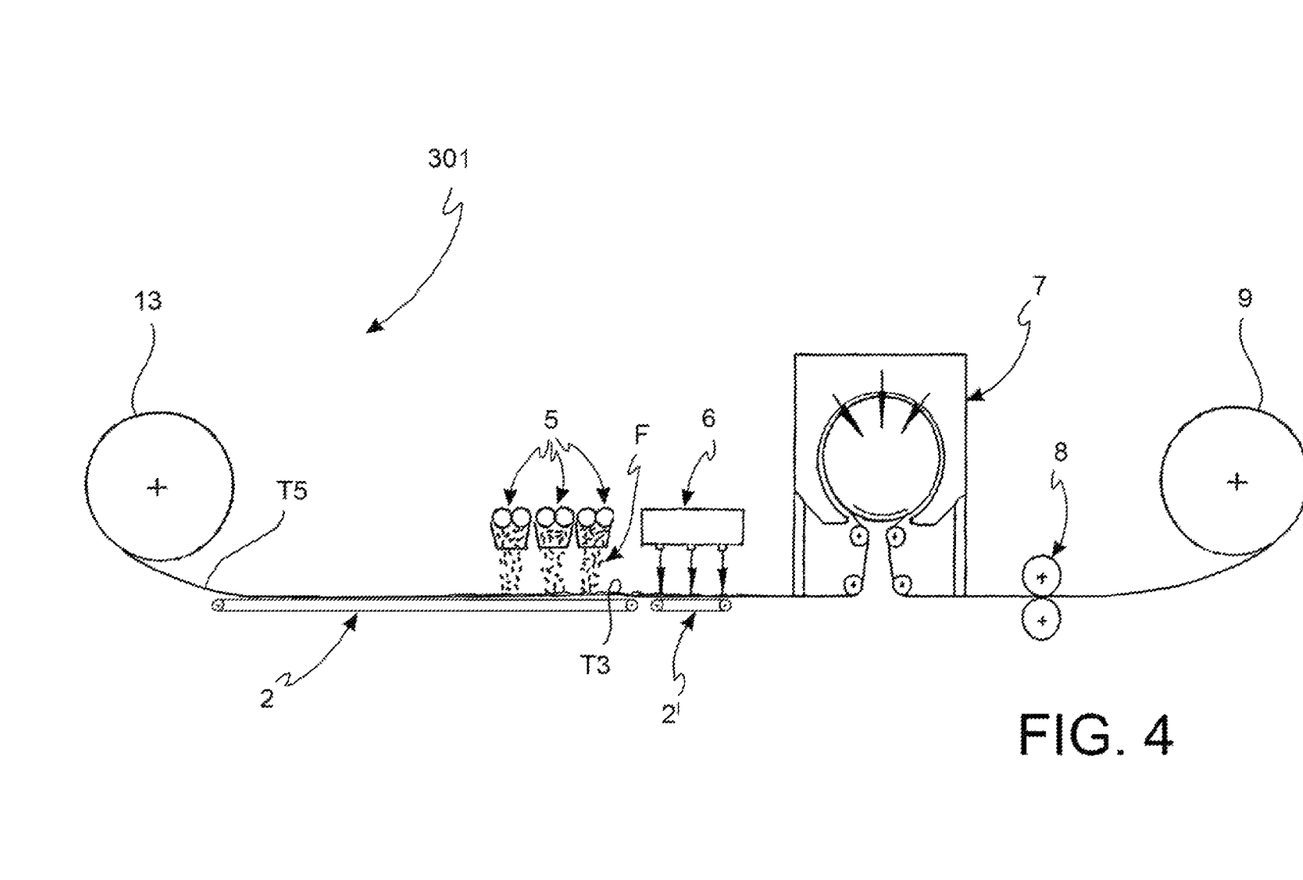
FIG. 4 illustrates by way of a schematic view a method for making nonwoven fabrics according to additional embodiments of the invention.

FIG. 4 shows a fourth embodiment of a production line 301 for manufacturing materials according to the present invention.

On transporting elements 2, such as a conveyor belt, a web T5 of a biopolymer as described above may be deposited by a bobbin 13.

Subsequently, water-absorbent, short fibers F, such as cellulose pulp fibers, may be deposited through suitable dispensing elements 5 to form a layer T3.

The web structure so-created may include from about 40 to about 50% by weight of the biopolymer and from about 50 to about 40% by weight of water-absorbent, short fibers.

After deposition of water-absorbent, short fibers, the layered material may be passed on to second transporting elements 2' through hydroentangling processes 6 such as those of a conventional type.

Bonded nonwoven fabric then may be dried passing through drying elements 7.

Dried nonwoven fabric may be subjected to calendering by the calender 8 which may have the calendering pattern such as that shown in FIG. 7.

Finally, bonded nonwoven fabric materials may be wound on a receiving bobbin 9.

Figure 5:
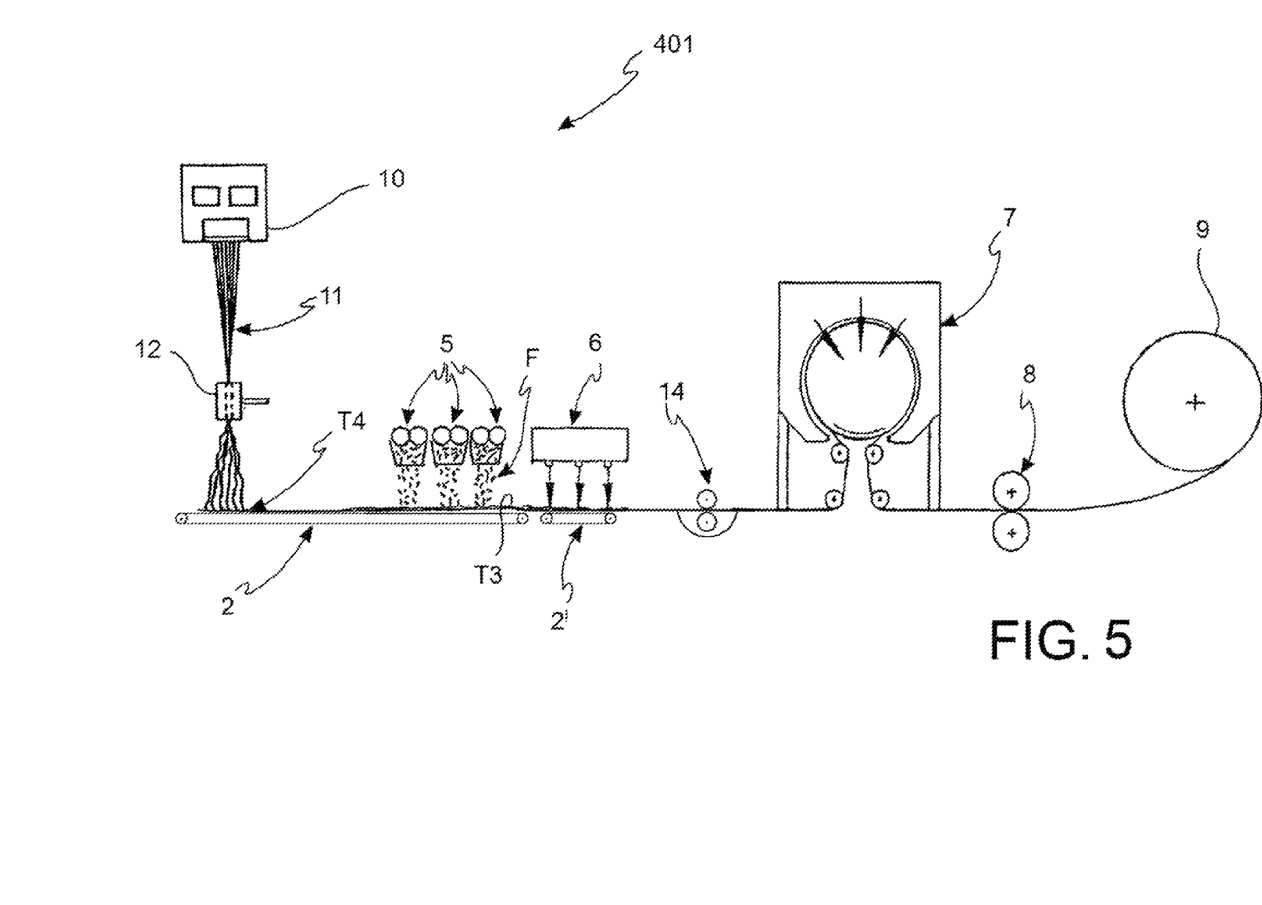
FIG. 5 illustrates by way of a schematic view a method for making nonwoven fabrics according to alternative embodiments of the invention.

FIG. 5 shows a fifth embodiment of a production line 401 for manufacturing the materials according to the present invention.

On transporting elements 2, such as a conveyor belt, a layer T4 of continuous filaments as described above (e.g. PLA spunlaid filaments) may be deposited after being extruded by a suitable spinneret 10. The threads 11 exiting the orifices of the spinneret 10 may be made to pass through a suction fan 12 positioned underneath the spinneret 10, in order to suck and convey the individual threads of extruded polymer.

Subsequently, water-absorbent, short fibers F, such as cellulose pulp fibers, may be deposited through suitable dispensing elements 5 to form a layer T3.

The web structure so-created may include from about 40 to about 50% by weight of continuous filaments and from about 50 to about 40% by weight of water-absorbent, short fibers.

The layered material then may be passed on to second transporting elements 2' through hydroentangling processes 6 such as those of a conventional type.

The bonded web may be passed through an applicator 14 to provide it with a hydrophilic treatment.

The bonded nonwoven fabric then may be dried passing through drying elements 7.

The dried nonwoven fabric may be subjected to calendering by the calender 8 which may have the calendering pattern such as that shown in FIG. 7.

Finally, the bonded nonwoven fabric material may be wound on a receiving bobbin 9.

Figure 6:
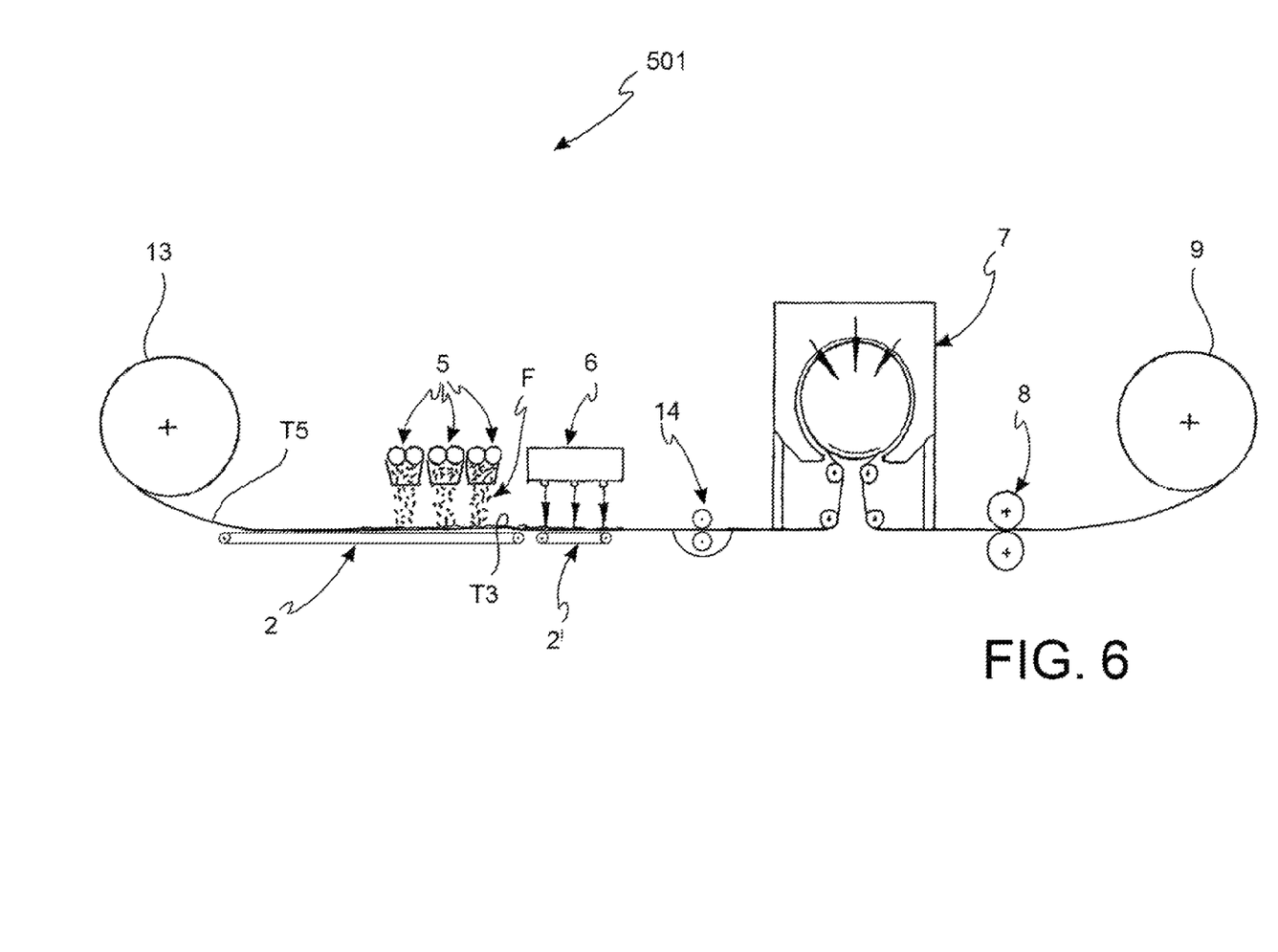
FIG. 6 illustrates by way of a schematic view a method for making nonwoven fabrics according to further alternative embodiments of the invention.

FIG. 6 shows a sixth embodiment of a production line 501 for manufacturing the materials according to the present invention.

On transporting elements 2, such as a conveyor belt, a web T5 of a biopolymer as described above may be deposited by a bobbin 13.

Subsequently, water-absorbent, short fibers F, such as cellulose pulp fibers, may be deposited through suitable dispensing elements 5 to form a layer T3.

The web structure so-created may include from about 40 to about 50% by weight of the biopolymer and from about 50 to about 40% by weight of water-absorbent, short fibers.

After deposition of water-absorbent, short fibers, the layered material may be passed on to second transporting elements 2' through hydroentangling processes 6 such as those of a conventional type.

Bonded nonwoven fabric may be passed through an applicator 14 to provide it with a hydrophilic treatment.

The bonded nonwoven fabric then may be dried passing through drying elements 7.

The dried nonwoven fabric may be subjected to calendering by the calender 8 which may have a calendering pattern such as that shown in FIG. 7.

Finally, the bonded nonwoven fabric material may be wound on a receiving bobbin 9.

Nonwoven fabric materials according to the present invention may be wetted or moistened with several types of substances before packaging. The term "substance" as used herein may include solutions, suspensions, gels, emulsions or other wet formulations for personal care, household application or topic medical use or combinations thereof, as the case may be.

Non-limiting examples of substances for personal care include: solutions or lotions for personal hygiene and/or sanitization, skin creams, lotions or waxes, tanning creams or lotions, sunscreen formulations, insect repellent formulations, deodorants, perfumes, antibacterial, antiviral and/or antifungal formulations, make-up removing lotions or solutions and cosmetic products in general.

Non-limiting examples of substances for household application include: detergent solutions or emulsions, waxes for ceramic or wooden floors, waxes for wood furniture surfaces, surface disinfectants, antibacterial, antiviral and/or antifungal products for household use, metal polishing emulsions, solutions or creams and cleaning formulations in general.

Non-limiting examples of substances for topical medical use include: skin disinfectants, skin antibacterial, antiviral and/or antifungal substances, cicatrizing formulations and in general any drug formulation that can be administered by topical application, or sanitizing compositions for medical facilities, appliances or devices.

In particular, when the substance is a viscous substance as may be the case with emulsions, suspensions, gels, creams or waxes, the wetting agent should be particularly efficient at imparting hydrophilicity to nonwoven fabrics and to favor distribution of the substance in the wipe. In one embodiment, nonwoven fabric materials may be treated with an alkylpolyglucoside ester. Disodium cocopolyglucose sulphosuccinate may be used, due to its beneficial fluidifying effect.

The inventive web structure may be impregnated with such substances by any method, such as the ones described above for wetting treatment, with the proviso that in certain embodiments the impregnated nonwoven fabric products of the invention are packaged while still wet. In particular, delivery of the substance on the web by means of suitable nozzles can be advantageously used. Impregnation as well as spraying are suitable methods for solutions or lotions.

The inventive textile products may be, for example, in the form of cloths, rags and similar fabrics, wipes, etc.

The nonwoven fabric materials of the invention have numerous advantages over prior art materials.

For example, the present invention provides nonwoven fabrics that are soft and have a bulky appearance. A good thickness of the nonwoven fabric, particularly when the fabric is wet or moistened, is preferred because it provides an attractive appearance for customers. This feature is achieved by nonwoven fabric materials according to the present invention in particular when PLA is contained in an amount greater than 5% by weight, and in some embodiments greater than 10% by weight.

The presence of PLA in the materials also allows patterned design to be readily visible on wet products, which is also considered important for the appearance of consumer products.

Nonwoven fabric materials provided herein also have very good mechanical properties. For example, such materials have a good balance between tensile strength, both in the dry and in the wet state, and water dispersibility.

In certain embodiments, the use of PLA in amounts greater than 30% by weight may improve mechanical properties of the fabric in the wet state.

Table I below provides the results of four trials using different compositions of the material. In all cases, the fabric was manufactured using processes as described above, like or similar to that shown in FIG. 1, where feeding lines 3 & 4 are fed by a carded web with a blend of viscose and PLA, but without the calendaring step.

Percentages in Table 1 are expressed by weight.

The base weight was measured using test method WSP 130.1 (ISO reference 9073-1:1989).

The thickness was measured using test method WSP 120.6 (ISO reference 9073-2:1995).

The MD- and CD-tensile strengths were determined using test method WSP 110.4 (ISO reference 9073-3:1989).

TABLE I

|  | 1<br>45% pulp<br>36% visc.<br>18% PLA | 2<br>18% pulp<br>64% visc.<br>18% PLA | 3<br>18% pulp<br>18% visc.<br>64% PLA | 4<br>45% pulp<br>18% visc.<br>36% PLA |
|---|---|---|---|---|
| Base weight (g/m$^2$) | 54.5 | 57.4 | 55.9 | 56.5 |
| Dry Thickness | 0.51 | 0.48 | 0.56 | 0.53 |
| Wet Thickness | 0.50 | 0.50 | 0.53 | 0.47 |
| Dry MD-strength (N/5 cm) | 73.8 | 106.5 | 91.4 | 81.4 |
| Dry CD-strength (N/5 cm) | 21.7 | 34.1 | 31.3 | 28.3 |
| Wet MD-strength (N/5 cm) | 32.8 | 48.3 | 65.6 | 50.5 |
| Wet CD-strength (N/5 cm) | 11.0 | 17.6 | 21.7 | 17.9 |
| Dry MD/CD strength | 3.4 | 3.1 | 2.9 | 2.87 |
| Wet MD/CD strength | 2.98 | 2.74 | 3.02 | 2.82 |

The data reported in Table I show that passing from dry to wet fabric both the MD- and CD-tensile strength decrease. However, when the content of PLA is above 30% by weight, this decrease is smaller and good values of tensile strength are still achieved in the wet material.

In all instances, the MD/CD tensile strength ratio is about 3 or less, which reveals a very good balance between these strengths in both directions. As stated above, this feature allows the fabric to be resistant to tearing and/or ripping both during its manufacture (rips along the MD direction) and during a customer's extraction from the package (rips along the CD direction).

Figure 8:
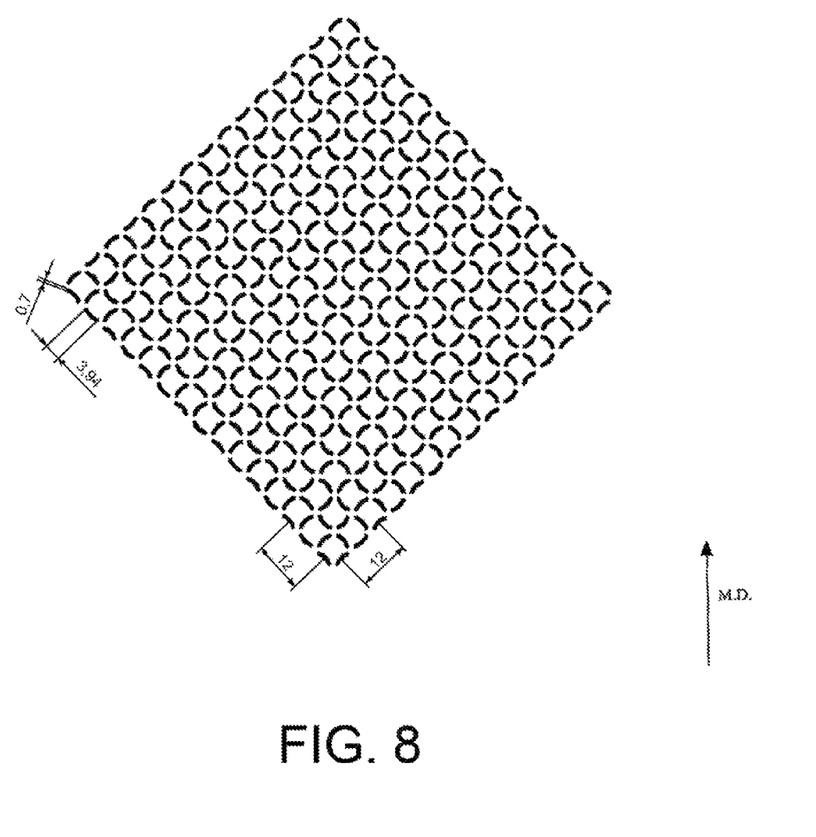
FIG. 8 illustrates an engraving pattern according to the prior art that is provided as a comparison.

Table II below provides a comparison between a nonwoven fabric material with the calendering pattern according to embodiments of the invention (FIG. 7) and the same material with a calendering pattern based on the prior art as shown in FIG. 8.

The data shown in Table 2 of the invention provides a MD/CD tensile strength ratio of 2.4 which is very advantageous compared with the prior art pattern, for which a value of 7.1 was measured.

This result is surprising, particularly for biodegradable, water-dispersible materials.

TABLE II

|  | 5 (invention)<br>60% viscose<br>40% cell. pulp | 6 (prior art)<br>60% viscose<br>40% cell. pulp |
|---|---|---|
| MD-tensile strength (N/5 cm) | 24.16 | 30.87 |
| CD-tensile strength (N/5 cm) | 10.12 | 4.35 |
| MD/CD ratio | 2.4 | 7.1 |

In fact, the calendering pattern according to embodiments of the invention involves the creation of bonding lines on the material to such an extent and orientation such that tensile resistance is imparted along all directions. However, this does not create adverse effects regarding the water-dispersibility of the fabric, because when the material is flushed and subject to a strong mechanical stress, such as in a pump turbine, the bonding lines work as breaking lines for the material, that is then cut into small pieces which can easily disperse.

Therefore, nonwoven fabric materials according to the present invention provide favorable and surprising balance between these properties.

It will be appreciated that only particular embodiments of the present invention have been described herein, to which those skilled in the art will be able to make modifications necessary for its adjustment to specific applications, without however departing from the scope of protection of the present invention as described and claimed herein.

The invention claimed is:

1. A method for making a nonwoven fabric material, the method comprising:
   a) depositing on a support at least one layer of a biodegradable material comprising long fibers or continuous filaments;
   b) hydroentangling the at least one layer and drying the hydroentangled material;
   c) calendering the dried material of step b) to create on the material a calendered pattern which provides a balanced ratio of MD/CD average tensile strength to the nonwoven fabric material, in a range between about 1:1 and about 4:1, wherein the calendering step is performed with a calender comprising ribs evenly alternating with grooves that define a calendering pattern thereon, wherein
   the calendering pattern of the calender comprises a plurality of ribs that are arranged in rows along the machine direction, each row forming first modules and second modules in alternate alignment, in each of the first modules the ribs being inclined with the same orientation, each first module being adjacent to two second modules having ribs being inclined with an opposite orientation, so that diagonal lines are defined joining corresponding points of the ribs in first modules or second modules, which diagonal lines define the inclined orientation of the ribs in such first modules or second modules, respectively, and wherein a first angle a is formed between the diagonal line defining the inclined orientation of the ribs in the first modules and the cross-direction, the first angle a being less than about 45 ° and a second angle is formed between the diagonal line defining the inclined orientation of the ribs in the second modules and the cross-direction, this second angle being supplementary to the first angle.

2. A method for making a nonwoven fabric material, the method comprising:
- a) depositing on a support at least one layer of a biodegradable material comprising long fibers or continuous filaments;
- b) hydroentangling the at least one layer and drying the hydroentangled material;
- c) calendering the dried material of step b) to create on the material a calendered pattern which provides a balanced ratio of MD/CD average tensile strength to the nonwoven fabric material, in a range between about 1:1 and about 4:1, wherein the calendering step is performed with a calender comprising ribs evenly alternating with grooves that define a calendering pattern thereon, wherein
- the ribs are formed in the shape of a stretched S with a first tract having a first curvature and a second tract having a second curvature being the opposite of the first curvature, the first and the second tracts being joined by a flexion point.

3. The method of claim 2, wherein the angle γ formed between a line tangential to one of the two ends of the rib and a line tangential to the flexion point is from about 15° to about 25°.

4. A method for making a nonwoven fabric material, the method comprising:
- a) depositing on a support at least one layer of a biodegradable material comprising long fibers or continuous filaments;
- b hydroentangling the at least one layer and drying the hydroentangled material;
- c) calendering the dried material of step b) to create on the material a calendered pattern which provides a balanced ratio of MD/CD average tensile strength to the nonwoven fabric material, in a range between about 1:1 and about 4:1, wherein the calendering step is performed with a calender comprising ribs evenly alternating with grooves that define a calendering pattern thereon, wherein the ribs have a height between about 0.5 and about 0.9 mm, a free head with a contact surface area for the fabric of from about 4 mm$^2$ to about 10 mm$^2$, and a distribution so that it covers about 6% to about 18% of the surface of the calender.

5. The method of claim 1, wherein the pitch between corresponding points of adjacent ribs in a same first or second module is between about 7 and about 12 mm.

6. The method of claim 1, wherein the pitch between corresponding points of ribs in two close first modules or in two close second modules is between about 8 and about 16 mm.

7. The method of claim 1, comprising a step of depositing on the said support or on the layer of step a) at least one layer of water-absorbent material before the hydroentanglement step b).

8. The method of claim 1, wherein the fibers are selected from the group consisting of: viscose, lyocell, polylactic acid (PLA), optionally as a bicomponent fiber, biopolymers from cereals or plant fibers and mixtures thereof; and wherein the continuous filaments are continuous filaments of polylactic acid (PLA).

9. The method of claim 1, wherein the water-absorbent material is selected from the group consisting of: cellulose pulp, cotton and mixtures thereof.

10. The method of claim 1, wherein the calendaring pattern comprises a plurality of dots of elongated shape which are interposed between the ribs in close rows of the first and second modules, respectively.

11. The method of claim 10, wherein the elongated dots are aligned along the MD direction or along the CD direction.

12. The method of claim 1, wherein the MD/CD average tensile strength ratio when the nonwoven fabric material is wet or moistened is between about 1:1 and about 2:1.

* * * * *